(12) United States Patent
Simonton et al.

(10) Patent No.: US 8,702,677 B2
(45) Date of Patent: Apr. 22, 2014

(54) DEVICE AND METHOD FOR DIRECTIONAL DELIVERY OF A DRUG DEPOT

(75) Inventors: Thomas A. Simonton, Memphis, TN (US); Sean M. Haddock, Memphis, TN (US); John Myers Zanella, Cordova, TN (US); William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 745 days.

(21) Appl. No.: 12/262,823

(22) Filed: Oct. 31, 2008

(65) Prior Publication Data

US 2010/0114075 A1    May 6, 2010

(51) Int. Cl.
*A61M 31/00* (2006.01)
*A61M 5/00* (2006.01)
*A61M 5/178* (2006.01)
*A61M 25/00* (2006.01)

(52) U.S. Cl.
USPC ........ 604/506; 604/57; 604/187; 604/164.01; 604/264

(58) Field of Classification Search
USPC .............. 424/426; 604/181, 264, 511, 892.1, 604/187, 500, 506, 507, 164.01, 272, 512, 604/57, 59, 60; 606/167, 213
See application file for complete search history.

(56) References Cited

U.S. PATENT DOCUMENTS

| | | | |
|---|---|---|---|
| 5,131,401 A | 7/1992 | Westenskow et al. | |
| 5,196,015 A | 3/1993 | Neubardt | |
| 5,391,081 A | 2/1995 | Lampotang et al. | |
| 5,466,219 A | 11/1995 | Lynn et al. | |
| 5,474,558 A | 12/1995 | Neubardt | |
| 5,830,130 A * | 11/1998 | Janzen et al. | 606/213 |
| 5,928,158 A | 7/1999 | Aristides | |
| 6,273,877 B1 | 8/2001 | West et al. | |
| 6,413,245 B1 * | 7/2002 | Yaacobi et al. | 604/264 |
| 6,554,778 B1 | 4/2003 | Fleming | |
| 6,993,375 B2 * | 1/2006 | Burbank et al. | 600/431 |
| 7,070,583 B1 | 7/2006 | Higuchi et al. | |

(Continued)

FOREIGN PATENT DOCUMENTS

EP       1625870 B1   5/2008
WO   2007121288 A2   10/2007

OTHER PUBLICATIONS

NIM-Eclipse(tm) Spinal System (2008 Medtronic Brochure) 4 pgs.

(Continued)

*Primary Examiner* — Bhisma Mehta
*Assistant Examiner* — Bradley G Thomas, Jr.
(74) *Attorney, Agent, or Firm* — Sorell Lenna & Schmidt LLP

(57) ABSTRACT

Drug depot delivery devices and methods are provided for delivering one or more drug depots to one or more sites beneath the skin of a patient with or without repositioning the cannula. The device has a cannula capable of insertion to the site beneath the skin of the patient and one or more side port openings for delivering a drug depot. The side port openings are spaced a distance from the blunt tip, which will allow the user to implant at a set distance from a nerve. The device may also include an electronic monitor for detecting the proximity of the tip of the cannula to a nerve. In some embodiments, a method of delivering a drug depot is provided by detecting the nerve and delivering the drug depot at or near the nerve.

24 Claims, 7 Drawing Sheets

(56) References Cited

U.S. PATENT DOCUMENTS

| | | |
|---|---|---|
| 7,125,425 B2 | 10/2006 | Foley et al. |
| 7,212,865 B2 | 5/2007 | Cory |
| 7,400,930 B2 | 7/2008 | Sharkey et al. |
| 2002/0116022 A1* | 8/2002 | Lebouitz et al. ............... 606/167 |
| 2003/0045808 A1 | 3/2003 | Kaula et al. |
| 2004/0015149 A1* | 1/2004 | Palasis .......................... 604/506 |
| 2004/0228901 A1 | 11/2004 | Trieu et al. |
| 2007/0118142 A1 | 5/2007 | Krueger et al. |
| 2007/0243228 A1* | 10/2007 | McKay ......................... 424/426 |
| 2007/0255281 A1 | 11/2007 | Simonton et al. |
| 2007/0255282 A1 | 11/2007 | Simonton et al. |
| 2007/0260184 A1 | 11/2007 | Justis et al. |
| 2007/0260201 A1 | 11/2007 | Prausnitz et al. |
| 2008/0004570 A1 | 1/2008 | Simonton et al. |
| 2008/0004703 A1 | 1/2008 | Trieu et al. |
| 2008/0065029 A1* | 3/2008 | Racz ............................. 604/272 |
| 2008/0102097 A1 | 5/2008 | Zanella |
| 2008/0139877 A1 | 6/2008 | Chu et al. |
| 2009/0131908 A1* | 5/2009 | McKay ......................... 604/511 |

OTHER PUBLICATIONS

NIM-Spine® System Pedicle Probe Technique (2007 Medtronic Brochure) 4 pgs.
NIM-Spine® System Neural Integrity Monitor Connection Procedure (2007 Medtronic Brochure) 12 pgs.
NIM-Spine® System Neural Integrity Monitor (2007 Medtronic Brochure) 4 pgs.
NIM-Knowledge Press Electricity in the Body (2007 Medtronic Brochure) 2 pgs.

* cited by examiner

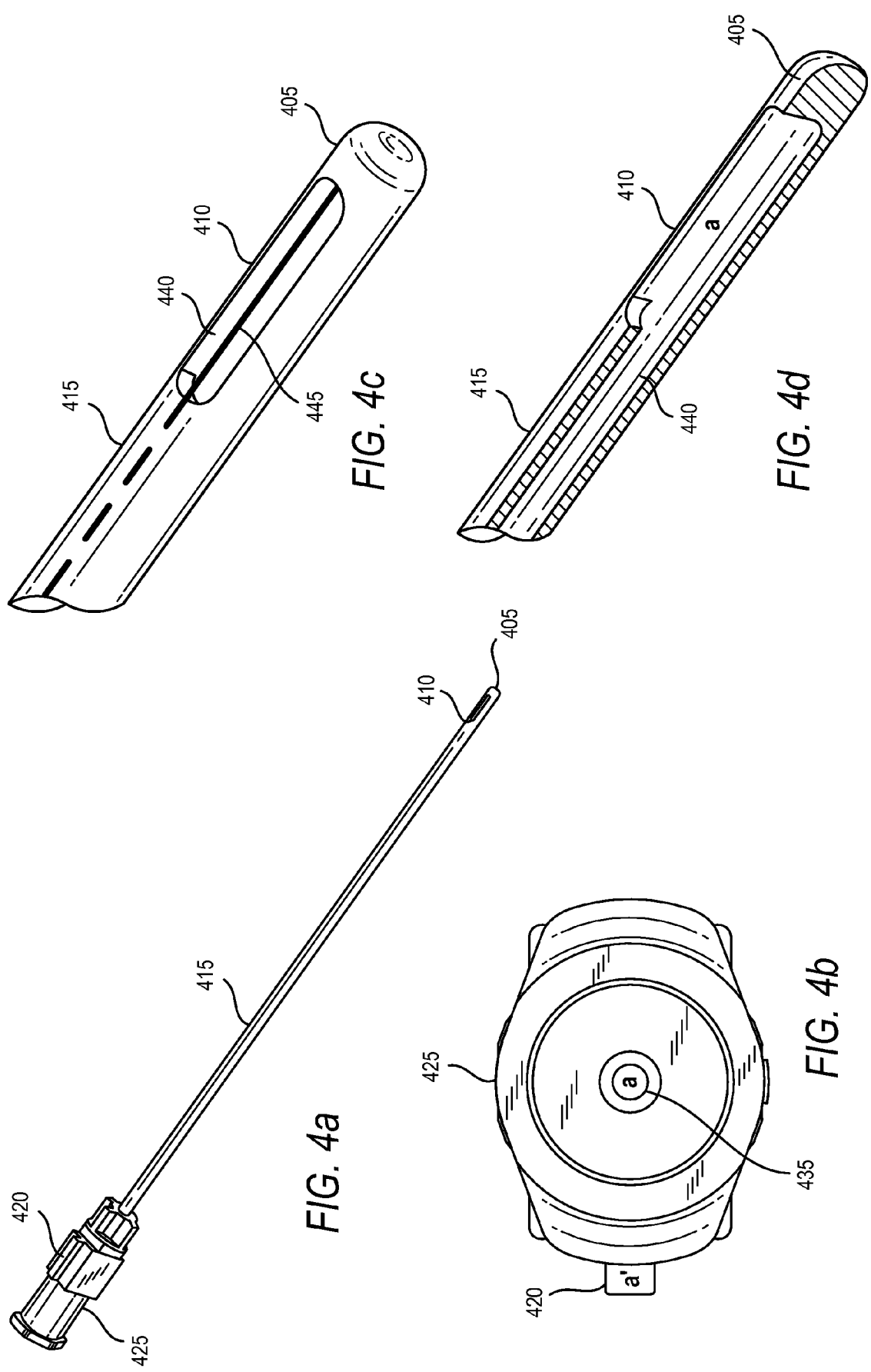

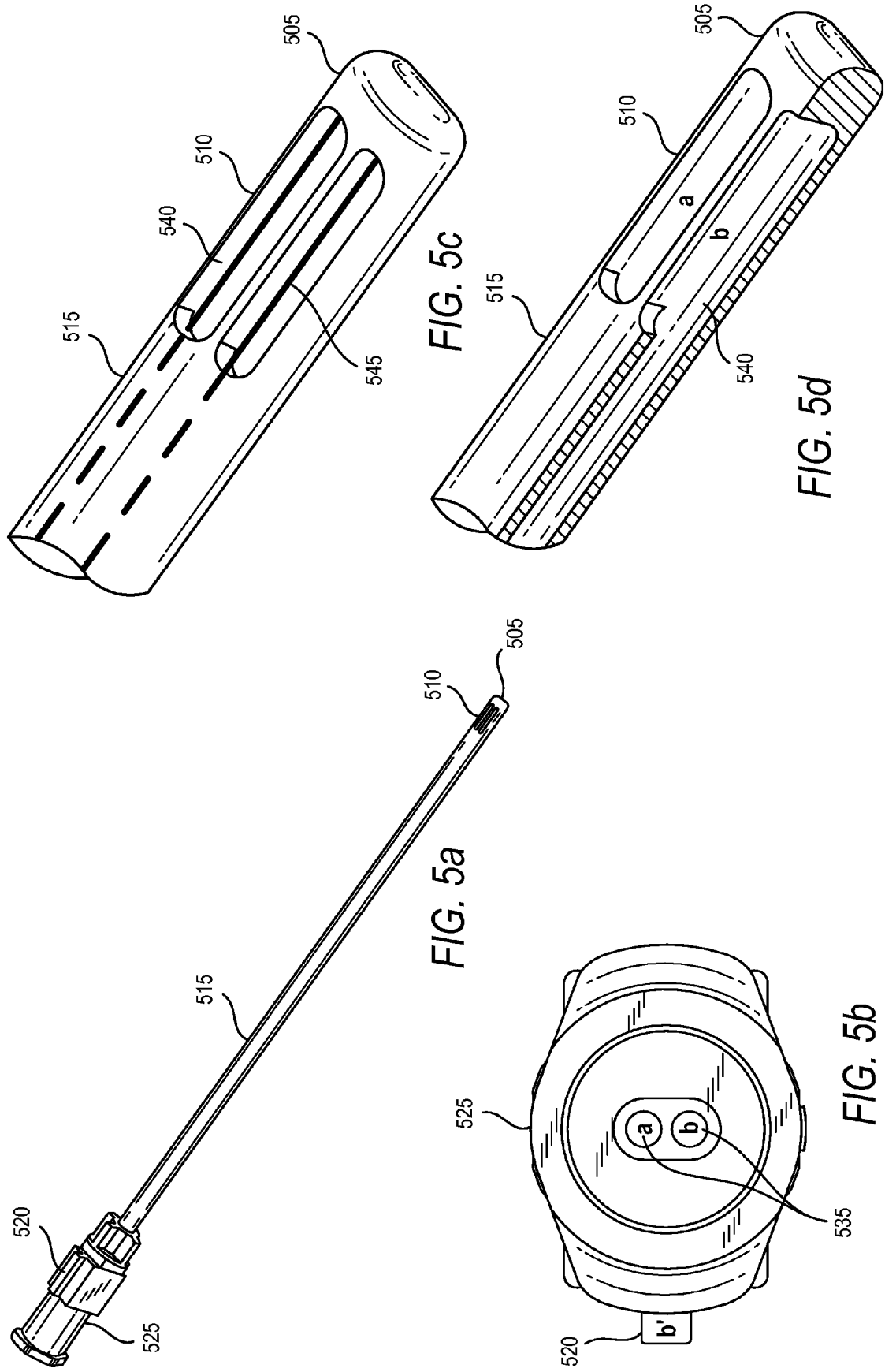

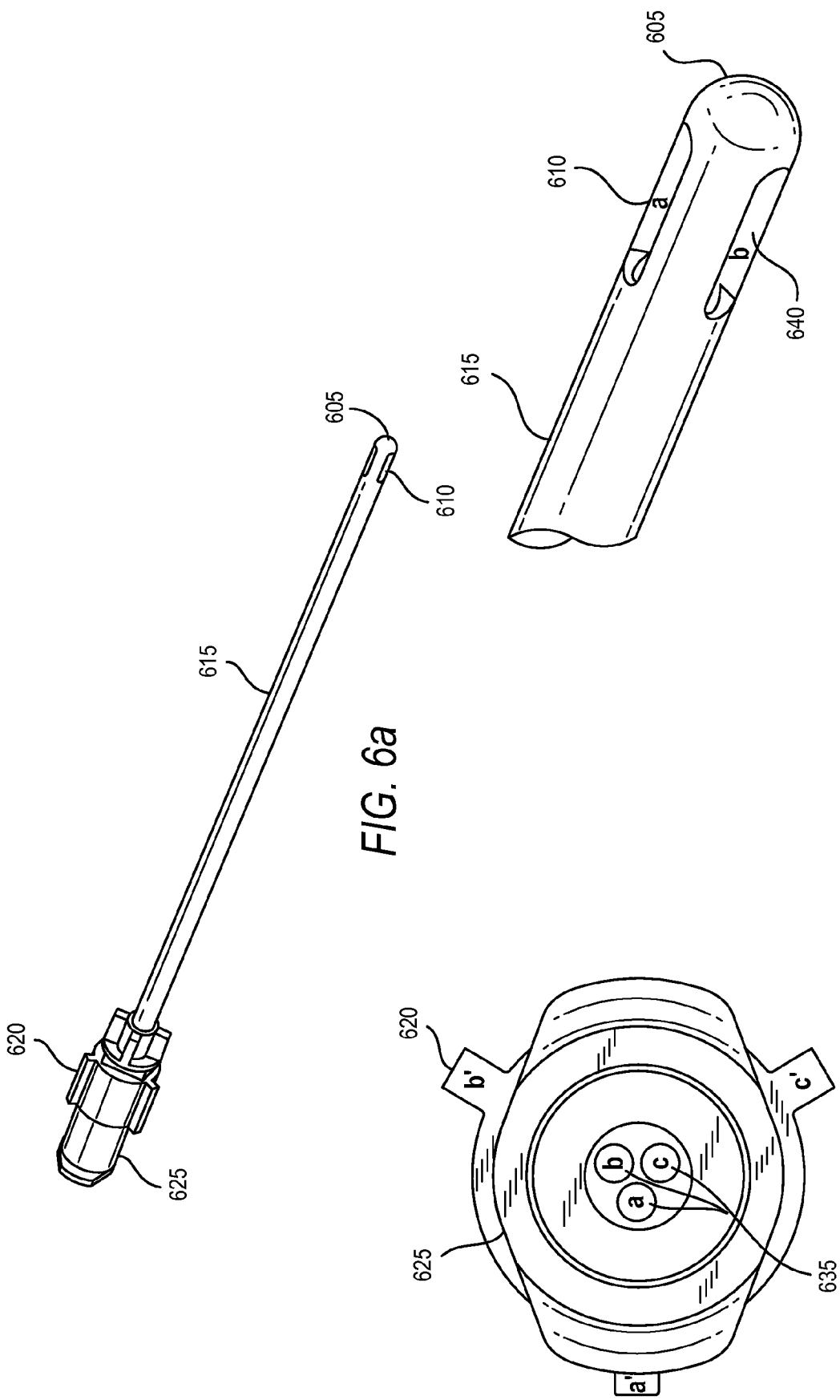

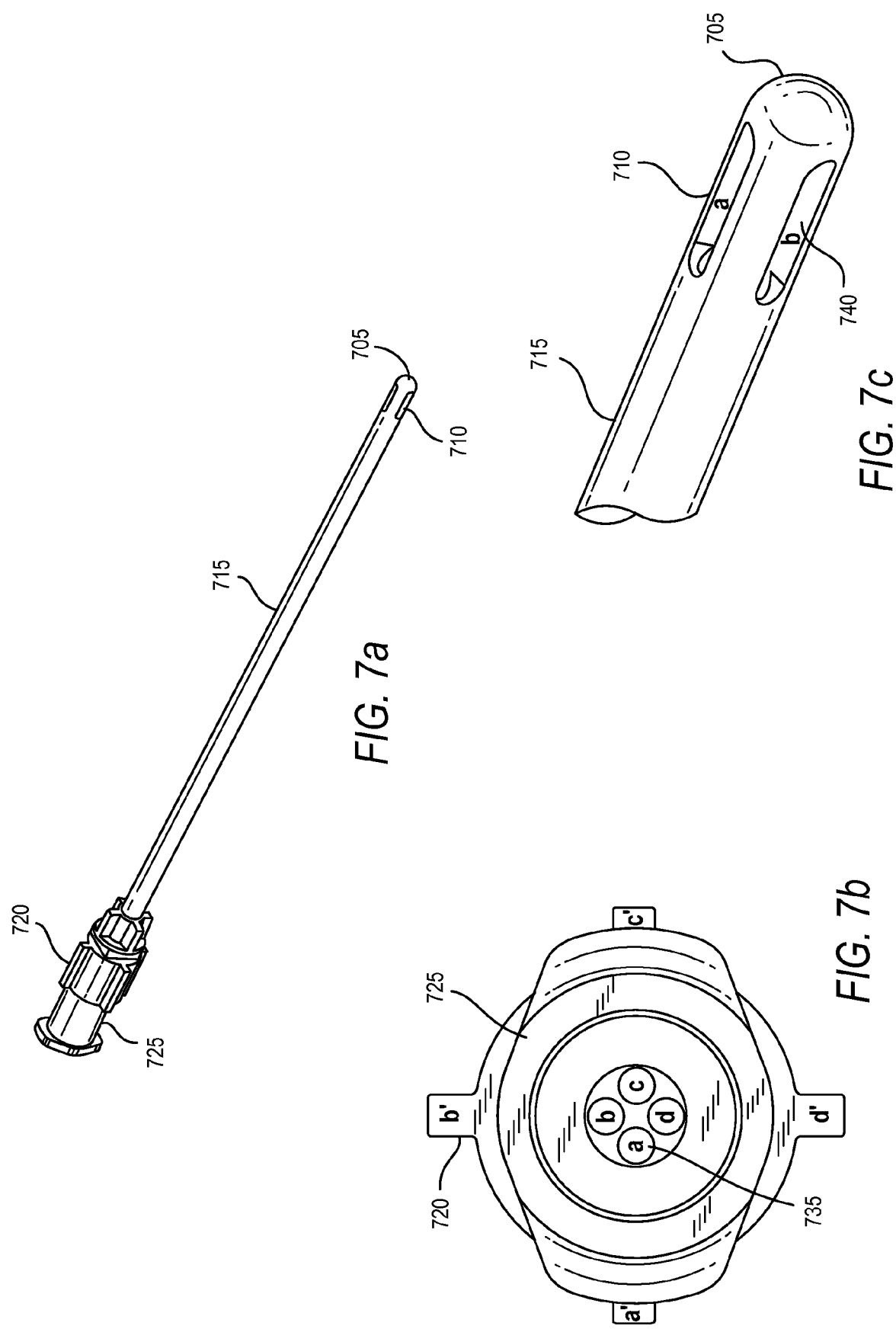

DEVICE AND METHOD FOR DIRECTIONAL DELIVERY OF A DRUG DEPOT

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain, and pain associated with injury or repair of cervical, thoracic, and/or lumbar vertebrae or intervertebral discs, rotator cuff, articular joint, TMJ, tendons, ligaments, muscles, and the like.

Previously, drug depots and other types of implants have been inserted into the treatment site beneath the skin by use of a trocar device, which is a two-piece device that includes a cannula and an obdurator. The trocar device requires an incision to be made through the skin at the site of implant of the drug depot using a separate instrument (e.g., scalpel). A cannula and obdurator are inserted together through the skin at the incision site. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the implant in place beneath the skin.

Typically, trocar devices are used to implant drug depots subcutaneously over a large area (e.g., 2-2.5 inches), with a typical drug depot in the order of 1½ inches long. Thus, the trocar device is not suitable for many treatment sites because it lacks precision, and may cause additional trauma to the tissue surrounding the site of implant.

Other drug depot devices have been developed to simplify implanting the drug depots. These devices have a handle for one-handed implantation of the drug depot, a needle containing the drug depot to be implanted and a rod positioned within the needle for pushing the drug depot out of the needle. Once the needle containing the drug depot has been inserted at the site of implant, a spring loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required.

Conventional needle and syringe devices have been used to implant a drug depot to sites such as, for example, the epidural space. These devices typically utilize a syringe preloaded with the drug depot and an epidural needle. The needle is inserted through the skin, supraspinus ligament, intraspinus ligament, ligamentum flavum and then into the epidural space. The drug depot is delivered through the needle to the epidural space using the syringe plunger. Conventional needle and syringe devices often do not easily allow controlled and precision implant of the drug depot. If multiple drug depot implants are needed, these conventional needle and syringe devices often do not allow accurate placement of the implant in a manner so that one drug depot does not substantially interfere with the dissolution of the other.

New drug depot devices are needed, which can easily allow accurate and precise implantation of a drug depot with minimal physical and psychological trauma to a patient. When implanting several drug depots, a drug depot device is needed that accurately and precisely allows placement of the drug depot in a manner such that one depot does not substantially interfere with the dissolution of the others.

SUMMARY

New drug depot devices which can easily allow accurate and precise implantation of a drug depot with minimal physical and psychological trauma to a patient are provided. One advantage of the drug depot device is that it allows the user to dispense multiple doses of the drug simultaneously or in sequence without having to reposition the needle. In some embodiments, the drug depot device comprises a blunt tip that allows the user to detect the nerve or whether the blunt tip is in close proximity to the nerve so that the user can avoid damaging the nerve. In some embodiments, the tip and/or housing of the device comprises an electrical sensor that will indicate when the tip of the needle is in close proximity to the nerve or contacts the nerve. In this way, the device allows the user to implant a drug depot close to the nerve and in some embodiments, avoid injuring the nerve.

In one embodiment, a device is provided for directional placement of a drug depot at a delivery site beneath the skin of a patient, the device comprising: a cannula having a proximal end and a distal end, the proximal end of the cannula having an opening to receive the drug depot, the distal end of the cannula capable of insertion to the delivery site beneath the skin of the patient and having a side port opening for passage of the drug depot, wherein the proximal end further comprises an index marker to provide a visual indicator to a user of a location of the side port opening; a housing having a coupling means for coupling the housing to the proximal end of the cannula and a storage component configured for storing the drug depot; and a plunger having a handle and a tip adapted for dispensing the drug depot, wherein the tip of the plunger is slidably receivable within each of the housing, storage component and the cannula to deliver the drug depot out the side port opening to the delivery site beneath the skin of the patient.

In another embodiment, a device is provided for directional placement of a drug depot at a delivery site beneath the skin of patient, the device comprising: a cannula having a proximal end and a distal end, the proximal end of the cannula having an opening to receive the drug depot and a nerve sensing unit comprising an electrical contact and an alarm coupled to the nerve sensing unit, the distal end of the cannula capable of insertion to the delivery site beneath the skin of the patient and having a side port opening for passage of the drug depot, wherein when the distal end of the cannula is in close proximity to a nerve or contacts a nerve, the alarm is activated; and a plunger having a handle and a tip adapted for dispensing the drug depot, wherein the tip of the plunger is slidably receivable within the cannula to deliver the drug depot out the side port opening to the delivery site beneath the skin of the patient.

In yet another embodiment, a method is provided for directional placement of a drug pellet to a site beneath the skin, the method comprising: positioning a cannula at the site beneath the skin, the cannula having a proximal end and a distal end, the proximal end of the cannula having an opening containing a drug pellet and a nerve sensing unit comprising an electrical contact and an alarm coupled to the nerve sensing unit, the distal end of the cannula capable of insertion to the site beneath the skin of the patient and having a side port opening for passage of the drug pellet and a blunt tip spaced a distance from the side port opening of the distal end of the cannula, wherein when the blunt tip is in close proximity to a nerve or contacts a nerve, the alarm is activated; and inserting a plunger into the proximal opening of the cannula, the plunger having a handle and a tip adapted for delivering the drug pellet from the side port opening of cannula, wherein the tip of the plunger is slidably receivable within the cannula to deliver the drug pellet out of the side port opening to the site beneath the skin of the patient.

In one exemplary embodiment, a method is provided for delivering a drug depot at or near a nerve site beneath the skin of a patient, the method comprising: providing a device for delivering a drug depot, the device comprising a cannula having a proximal end and a distal end, the proximal end of the cannula having an opening to receive the drug depot, the distal end of the cannula capable of insertion to the nerve site beneath the skin of the patient and having an opening for passage of the drug depot; a plunger being slidably receivable within the opening of the proximal end of the cannula, the plunger having a first end and a tip at a second end, the first end being capable of moving the tip of the plunger to an extended position; a nerve sensor disposed within the device, the nerve sensor configured to receive electrical impulses from the nerve site so as to detect the nerve, inserting the distal end of the cannula and/or the plunger at or near the nerve site beneath the skin of the patient and detecting the nerve site; loading the drug depot for delivery in the cannula; and positioning the plunger within the cannula and moving the plunger in the extended position thereby delivering the drug depot from the distal end of the cannula at or near the nerve site beneath the skin of the patient.

In another embodiment, a method is provided for delivering a drug depot at or near a nerve site beneath the skin of a patient, the method comprising: providing a device for delivering a drug depot, the device comprising a cannula having a proximal end and a distal end, the proximal end of the cannula having an opening to receive the drug depot, the distal end of the cannula capable of insertion to the nerve site beneath the skin of the patient and having an opening for passage of the drug depot; a plunger being slidably receivable within the opening of the proximal end of the cannula, the plunger having a first end and a tip at a second end, the first end being capable of moving the tip of the plunger to an extended position; a nerve sensor disposed within the device comprising an electrical contact and an alarm coupled to the nerve sensor, the nerve sensor configured to receive electrical impulses from the nerve site so as to detect the nerve, inserting the distal end of the cannula and/or the plunger at or near the nerve site beneath the skin of the patient and detecting the nerve site; loading the drug depot for delivery in the cannula; and positioning the plunger within the cannula and moving the plunger in the extended position thereby delivering the drug depot from the distal end of the cannula at or near the nerve site beneath the skin of the patient.

In yet another exemplary embodiment, a device is provided for delivery a drug depot at or near a nerve site beneath the skin of a patient, the device comprising: a cannula having a proximal end and a distal end, the proximal end of the cannula having an opening to receive the drug depot, the distal end of the cannula capable of insertion to the nerve site beneath the skin of the patient and having an opening for passage of the drug depot; a plunger being slidably receivable within the opening of the proximal end of the cannula, the plunger having a first end and a tip at a second end, the first end being capable of moving the tip of the plunger to an extended position; a nerve sensor disposed on or within the device, the nerve sensor comprising an electrical contact material configured to receive electrical impulses from the nerve site so as to detect the nerve.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 4a illustrates an exemplary embodiment of a cannula of a drug delivery device having a single side port and a blunt tip at the distal end of the cannula for delivering a drug depot to a delivery site.

FIG. 4b illustrates an exemplary embodiment of the top view of the proximal end of a cannula having a single opening or chamber for depositing a drug depot for delivery through the cannula to a delivery site, the opening also configured to receive a plunger to facilitate the delivery of the drug depot.

FIG. 4c illustrates an exemplary embodiment of the distal end of a cannula having a single side port for delivering a drug depot at a delivery site.

FIG. 4d illustrates an exemplary embodiment of the cross-section view of a cannula having a single inner chamber for delivering a drug depot through a single side port.

FIG. 5a illustrates an exemplary embodiment of a cannula of a drug delivery device having a double port at the distal end of the cannula for delivering multiple drug depots to a delivery site.

FIG. 5b illustrates an exemplary embodiment of the top view of the proximal end of a cannula having a double opening or chamber for depositing multiple drug depots for delivery through the cannula to a delivery site, the opening also configured to receive a plunger configured to facilitate the delivery of the drug depots.

FIG. 5c illustrates an exemplary embodiment of the distal end of a cannula having a double side port for delivering multiple drug depots at a delivery site.

FIG. 5d illustrates an exemplary embodiment of the cross-section view of a cannula having two inner chambers for delivering multiple drug depots through a two side port opening.

FIG. 6a illustrates an exemplary embodiment of a cannula of a drug delivery device having a triple side port opening at the distal end of the cannula and a blunt tip for delivering multiple drug depots to a delivery site.

FIG. 6b illustrates an exemplary embodiment of the top view of the proximal end of a cannula having a triple opening for depositing multiple drug depots for delivery through the cannula to a delivery site, the opening also configured to receive a plunger configured to facilitate the delivery of the drug depots.

FIG. 6c illustrates an exemplary embodiment of the distal end of a cannula having a triple side port opening for delivering multiple drug depots at a delivery site.

FIG. 7a illustrates an exemplary embodiment of a cannula of a drug delivery device having a quadruple side port opening and a blunt tip at the distal end of the cannula for delivering multiple drug depots to a delivery site.

FIG. 7b illustrates an exemplary embodiment of the top view of the proximal end of a cannula having a quadruple side port opening for depositing multiple drug depots for delivery through the cannula to a delivery site, the opening also configured to receive a plunger configured to facilitate the delivery of the drug depots.

FIG. 7c illustrates an exemplary embodiment of the distal end of a cannula having a quadruple side port opening for delivering multiple drug depots at a delivery site. The distal end of the cannula has a blunt tip.

Figure 1:
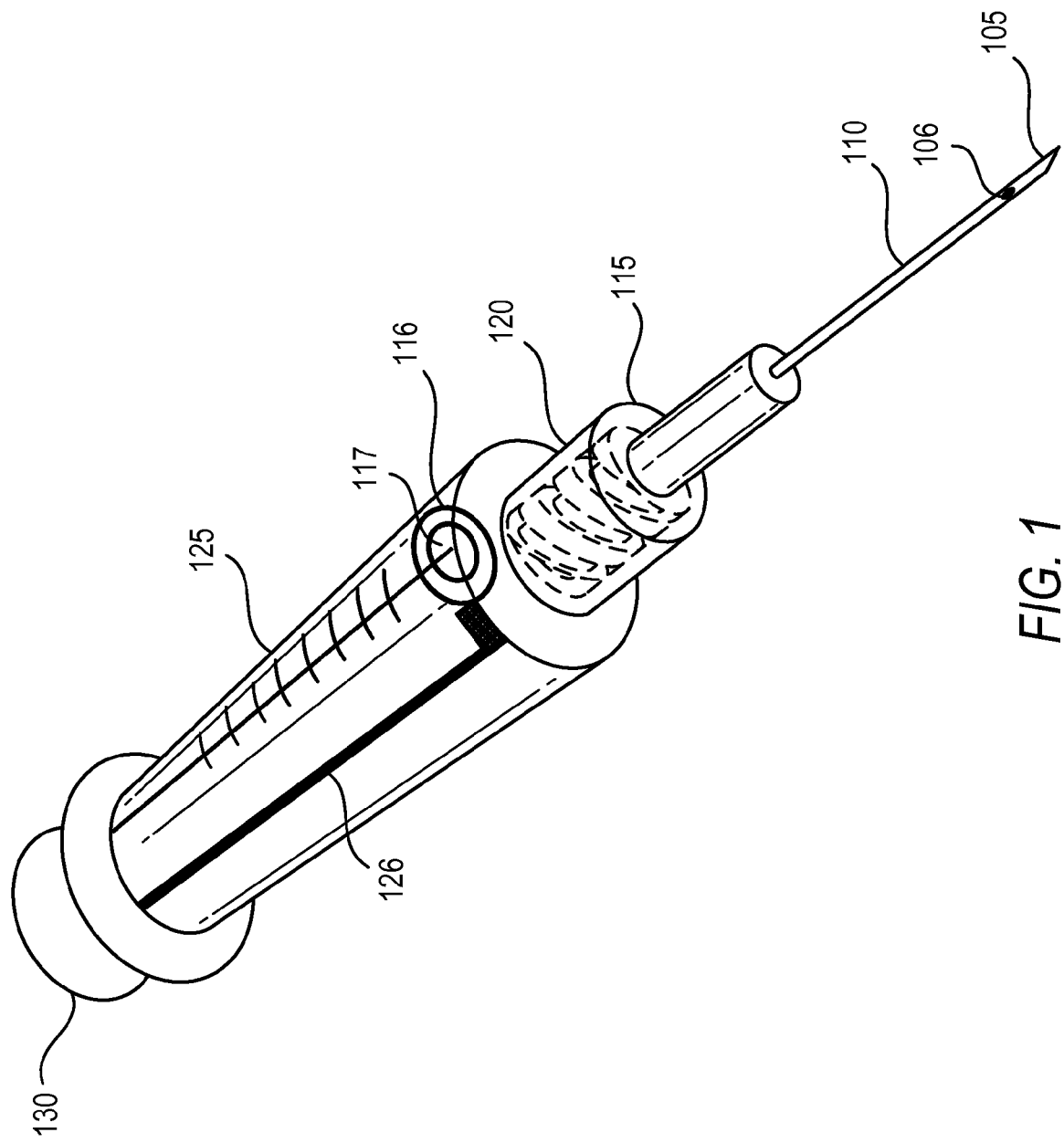
FIG. 1 illustrates an exemplary embodiment of a drug delivery device having a cannula, a housing, a sensor to detect the nerve, and a plunger for delivering the drug depot to a delivery site.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1, and a maximum value, of equal to, or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug depot devices, which can easily allow accurate and precise implantation of a drug depot with minimal physical and psychological trauma to a patient are provided. One advantage of the drug depot device is that it allows the user to dispense multiple doses of the drug simultaneously or in sequence without having to reposition the needle. In some embodiments, the drug depot device comprises a blunt tip that allows the user to detect the nerve or whether the blunt tip is in close proximity to the nerve so that the user can avoid damaging the nerve. In some embodiments, the tip and/or housing of the device comprises an electrical sensor that will indicate when the tip of the needle is in close proximity to the nerve. For example, the electrical sensor will indicate when the tip of the needle is within 1 mm of the nerve or makes contact with the nerve. In this way, the device allows the user to avoid injuring the nerve.

FIG. 1 illustrates an embodiment of an assembled drug delivery device comprising a cannula 110 and a plunger 130 connected via a housing 125. In various embodiments, the cannula has a proximal end 115 and a distal end having a tip 105 (shown as a beveled tip). The tip at the distal end of the cannula is capable of insertion to a site beneath the skin and the proximal end of the cannula is capable of engaging a housing. Spaced apart from the tip of the cannula 105 is a side port opening 106 that is a sufficient size to allow a drug depot to pass therethrough to the delivery site. Since the spacing between the side port and the tip is known (e.g., 1, 2, 3, 4, 5 mm apart), when the user contacts, for example, the nerve with the tip, the user will know that the side port(s) is 1, 2, 3, 4, 5 mm away from the nerve and can implant the drug depot at a set distance from the nerve. In this way, the blunt tip is used as a probe for the user to manually gauge the distance from the nerve to implant the drug depot. In various embodiments, the proximal end of the cannula is engaged to the housing with a coupling means 120, wherein the coupling means can be a luer lock, threading, friction fit fitting, etc. In some embodiments, the housing has a sensor unit, e.g. a nerve sensing unit 116 that is electrically coupled to an electrical contact (not shown) at the distal end of the cannula to indicate close proximity to a nerve and an alarm 117 to alert the user of close proximity of the tip to the nerve. In various embodiments the sensor unit is electrically coupled, via electrical wire 126, to for example, a power supply, user control switches, a stimulation device, and/or an external monitoring device (exemplary devices not shown). When the tip approaches a nerve or contacts a nerve tissue, the alarm 117 will sound (e.g., buzzer, bell, etc.) or show a visual signal (e.g., light, LED, LCD, etc.) to alert the user.

In some embodiments, the nerve sensing unit may comprise a wire or other electrical conductive material (e.g., metal) running from the tip or distal end of the cannula to a sound and/or visual device that conducts the electrical impulses (e.g., 40 to 90 millivolts (mV)) from the nerve to the sound and/or visual device. In this embodiment, as the user contacts the nerve with the blunt tip of the cannula, the nerve impulse will be conducted through the cannula, through the wire and to the sound and/or visual device, which will alert that user with a visual and/or audio signal that the tip has now contacted a nerve. In this way, deposit of the pellets in close proximity of the nerve is ensured.

In various embodiments, the drug depot is placed at the target tissue site often using diagnostic imaging procedures, such as for example, X-ray imaging, fluoroscopy, etc. However, the nerve roots do not show up during the procedure. The devices and methods provided allow the user to detect the nerve with the tip of the cannula or needle and implant the drug depot next to the nerve, where it can provide its local therapeutic effect.

In various embodiments, the cannula is hollow having a sufficient diameter to allow passage of a drug depot and the plunger that facilitates delivery of the drug depot to the designated site beneath the skin. The plunger can have a knob, or gripping features that enable the user to move the plunger in order to deliver the drug depot. The housing may also have grips for the user to hold the housing and connect the cannula to it. The size of the cannula is dictated by the type of drug depot to be delivered and the procedure to be performed.

Figure 2:
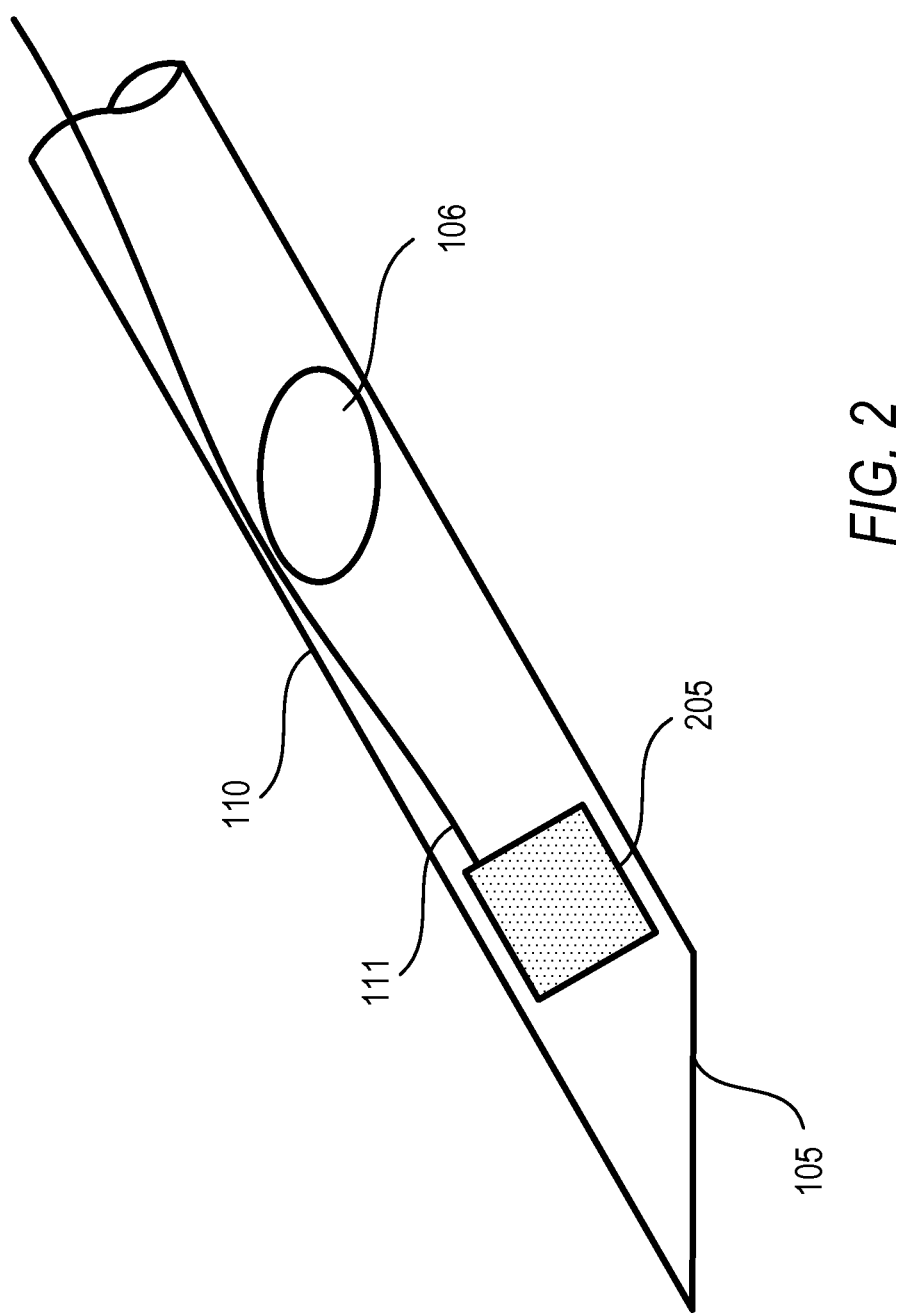
FIG. 2 illustrates an exemplary embodiment of a cannula having a side port at the distal end of the cannula near the tip and a sensor to detect proximity to a nerve.

FIG. 2 illustrates an embodiment of an expanded view of the distal end of the cannula shaft 110 of a drug delivery device comprising a tip 105 having a side port 106 for dispensing the drug depot at a delivery site. The distal end of the cannula also has an electrical contact 205 that detects the electrical impulse generated by the nerve when the tip of the cannula 105 contacts the nerve. The electrical contact is electrically coupled via a wire 111 in order to send a signal to the alarm to let the user know that the tip of the cannula contacted or is near the nerve. In this way, the user can move the tip away from the nerve.

Figure 3:
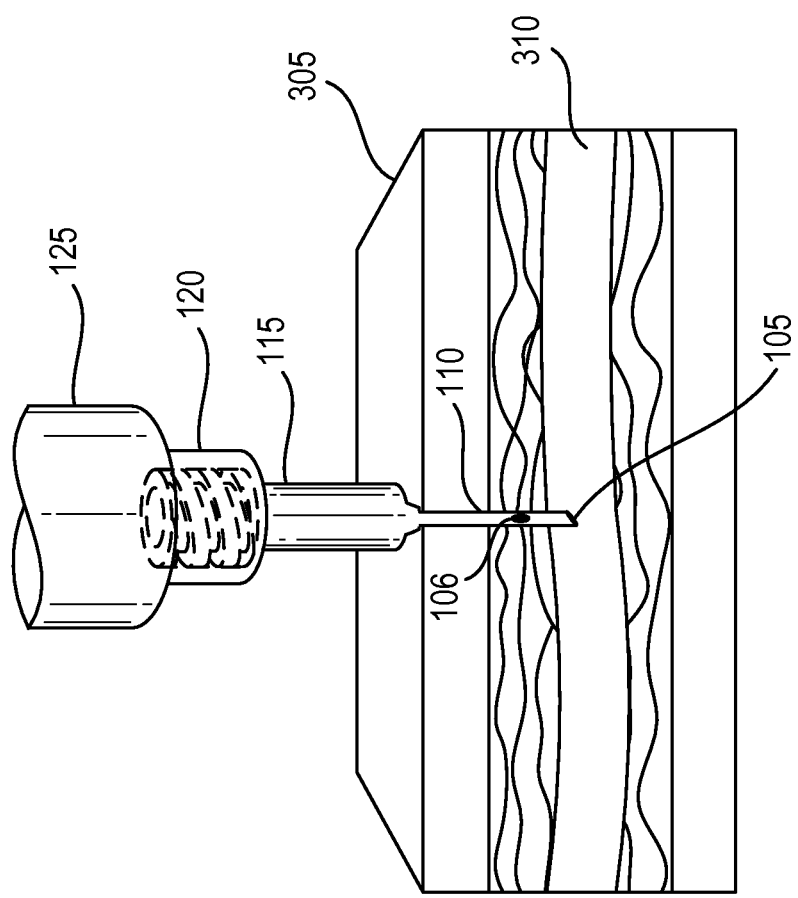
FIG. 3 illustrates an exemplary embodiment of a side sectional view of a drug delivery device inserted at a delivery site beneath the skin, where the device contacts nerve tissue.

FIG. 3 illustrates an embodiment of a drug delivery device having a cannula 110 inserted beneath the skin 305 to deliver the drug depot at a delivery site. The cannula is attached to the housing 125 (shown as a syringe barrel that can store the drug depot in a chamber). The housing can be connected to the cannula by threading or leur fitting 120. In this illustrated embodiment, the tip 105 is contacting a nerve 310. In embodiments, where the sensor is within the housing, the sensor will alert the user via an alarm (not shown) that the blunt tip 105 has contacted the nerve. In some embodiments, the user can monitor the depth of the blunt tip via diagnostic imaging procedures, such as for example, X-ray imaging, fluoroscopy, etc. and know when the nerve is contacted and the distance of the side port opening 106 from the nerve. Thus, the user can implant the drug depot in close proximity to the nerve. In this way, the user can implant the drug depot with precision.

FIG. 4a illustrates an embodiment of a single barrel cannula assembly for delivering a drug depot to a single delivery site. In various embodiments the single barrel cannula assembly comprises a blunt tip 405 at the distal end of the cannula, a side port 410 for dispensing the drug depot at the delivery site, a cannula shaft 415, an index marker 420 to indicate the position of the side port on the cannula shaft and its relative position beneath the skin. The index marker may be located at the proximal end 425 of the cannula assembly and it remains visible to the user during the procedure. The marker 420 will be aligned with and/or parallel to the side port opening so that the user will have a visual indicator of the index marker and can know in what direction the drug depot will be implanted at the delivery site.

FIG. 4b illustrates an embodiment of the top view of the proximal end 425 of a cannula assembly in the drug delivery device. In various embodiments, the proximal end has an opening or chamber 435 configured to receive a drug depot for delivery at a delivery site. In various embodiments, the index marker 420 protrudes from the cannula so that it is visible to the user throughout the procedure. Thus the chamber or channel for the drug depot shown as "a" in 435 will be parallel to the index marker a' and the user will know the position of the chamber and thus the drug depot by looking at the index marker a' of 420. The fitting of the proximal end of the cannula is shown as 425 and is configured to receive a plunger and/or a housing such as a drug cartridge.

FIG. 4c illustrates an embodiment of the cannula shaft 415. In various embodiments, the side port 410, at the distal end of the cannula, is some distance away from the tip of the cannula 405. In various embodiments the distance between the side port and the tip may be between 1-10 mm. In various embodiments the shaft of the cannula is hollow creating a chamber 440 for the passage of the drug depot to the delivery site. In various embodiments, a plunger 445 slides within the cannula and may be used as a guide to slide the drug depot through the cannula shaft and out the side port to the drug delivery site. Again, since the spacing of the side port opening from the blunt tip is known, the user will know the exact distance of implantation from the nerve of the drug depot. Thus, the user can implant the drug depot a set distance from the nerve, which will be beneficial to the patient as the drug can be locally delivered to the area, without injury to the nerve. In FIG. 4c, the plunger is shown in the extended position.

FIG. 4d illustrates a cross-sectional view of an embodiment of a cannula shaft 415, having an inner chamber or channel 440 for passing the drug depot from the proximal end of the cannula to the distal end of the cannula, when the plunger is aligned in the chamber or channel. The passage way for the drug depot is indicated by the "a" and the entrance for the drug depot begins with the chamber or channel marked with an "a" in FIG. 4 b. Thus, the entrance of chamber or channel "a" will be aligned from the entrance to the side port opening 415 (shown as an a) and create a passage for the drug depot to be pushed out by the plunger and dispensed at the delivery site. The user will know the position of the drug depot by also viewing the index marker (420 a' in FIG. 4b).

FIG. 5a illustrates an embodiment of a double barrel cannula assembly for delivering two drug depots to two delivery sites. In various embodiments, the double barrel cannula assembly comprises a blunt tip 505 at the distal end of the cannula, two side ports 510 for expelling the drug depots at the delivery sites, a cannula shaft 515, an index marker 520, to indicate the position of the side ports beneath the skin. The index marker may be located at the proximal end 525 of the cannula assembly and it remains visible to the user during the procedure. For example, in FIG. 5b, the index marker 520 can be parallel and at a point center to the drug chambers or channels indicated as a and b of 535. The index marker shown as 520 b' will be parallel and center to drug chambers or channel 535 a and b. By looking at index marker 520 b', the user will know the position of the drug chambers or channels a and b. The user will also know the position of the side port openings a and b (shown in of FIG. 5 d) and thus will know the angle that the drug depot will be dispensed and the position of the side port openings by viewing index marker 520 b'.

FIG. 5b also illustrates an embodiment of the top view of the proximal end 525 of a cannula assembly in the drug delivery device. In various embodiments, the proximal end has two openings or chambers 535 a and b, each configured to receive a drug depot for delivery at the delivery sites beneath the skin. In various embodiments, the index marker 520 protrudes from the cannula so that it is visible to the user throughout the procedure. The proximal end of the cannula has a coupling means 525 (e.g., luer fitting, friction fit fitting, threading, etc.) to connect to the housing or to receive a plunger.

FIG. 5c illustrates an embodiment of the cannula shaft 515. In various embodiments, the side ports 510 at the distal end of the cannula are some distance away from the tip of the cannula 505. In various embodiments the distance between the side port and the tip may be from 1, 2, 3, 4, 5, 6, 7, 8, 9, and 10 mm. In various embodiments, the shaft of the cannula is hollow creating two chambers or channels 540 (a and b) for the passage of the drug depots to the delivery sites. In various exemplary embodiments, a drug depot is inserted into opening 535, and would travel through the cannula shaft via chamber 540 and would be expelled through side port 510 at a first drug delivery site. In various embodiments, a plunger may be used to facilitate delivery of the drug depot through the cannula shaft and out the side port to the drug delivery site. In various embodiments having two chambers for dispensing two drug depots, the plunger would be appropriately configured to provide two plunging tips 545 that would slide one at a time in each chamber 540 or would simultaneously slide in both chambers because the plungers will have two tips which are in each chamber and dispense the drug depots through each of the side ports. In FIG. 5c, the plunger is shown in the extended position.

FIG. 5d illustrates a cross-sectional view of an embodiment of a cannula shaft 515, having two separate inner chambers 540, wherein each chamber (a and b) corresponds to an opening (a and b of FIG. 5b) at the proximal end for inserting a drug depot as well as a side port 510 at the distal end of the cannula. Each drug depot is contained within its respective chamber, isolated from contact with the adjacent drug depot in the adjacent chamber.

In various embodiments the cannula assembly may be such that the drug delivery sites may vary in position. For example, the drug delivery sites may be adjacent to one another (as illustrated in FIG. 5a), opposite each other (i.e., 180 degree separation), or at a right angle to each other (i.e., 90 degree separation).

FIG. 6a illustrates an embodiment of a triple barrel cannula assembly for delivering three drug depots to three different delivery sites. In various embodiments, the triple barrel cannula assembly comprises a blunt tip 605 at the distal end of the cannula, three side ports (two are shown as 610), each side port can dispense one or more drug depots when the plunger is slid therethrough to different delivery sites. The cannula shaft 615, index markers 620 are aligned with the chambers to indicate the positions of each of the side ports 610 beneath the skin such that the location of each of the three ports beneath the skin is represented by a corresponding index marker 620 located at the proximal end 625 of the cannula assembly visible to the user.

For example, in FIG. 6b, the index marker 620 can be parallel to the drug chambers or channels indicated as a, b, and c of 635. The index marker shown as 620, a', b' and c' will be parallel to each drug chamber or channel respectively (shown as 635 a, b, and c). By looking at index marker 620 a', 620 b', and 620 c', the user will know the position of the drug chamber or channel 635 a, 635 b, and 635 c, respectively. The user will also know the position of the side port openings a and b (shown in of FIG. 6 c) and thus will know the angle that the drug depot will be dispensed and the position of the side port openings by viewing index marker 620.

FIG. 6b also illustrates an embodiment of the top view of the proximal end 625 of a cannula assembly in the drug delivery device. In various embodiments, the proximal end has three openings 635 a, b, and c, each configured to receive a drug depot for delivery at the delivery sites beneath the skin. In various embodiments, the three index markers a', b' and c' protruding from the cannula are substantially parallel to each chamber (635 a, b, and c) so that they are visible to the user throughout the procedure.

FIG. 6c illustrates an embodiment of the cannula shaft 615. In various embodiments, the side ports 610 (two are shown as a and b, the other is not shown), at the distal end of the cannula, are some distance away from the tip of the cannula 605. In various embodiments, the distance between the side port and the cannula may be between 1-10 mm. In various embodiments, the shaft of the cannula is hollow creating three chambers or channels for the passage of the drug depots to the delivery sites. In various exemplary embodiments, a drug depot inserted into opening 635a of FIG. 6b, would travel through the cannula shaft via the chamber or channel and be dispensed through side port 610 a in FIG. 6c at a first drug delivery site. In various embodiments, a plunger may be used to facilitate delivery of the drug depot through the cannula shaft and out the side port to the drug delivery site. In various embodiments having three chambers or channels (a, b, and c in FIG. 6b) for dispensing three drug depots, the plunger would be appropriately configured to provide three plunging tips (not visible) to dispense the drug depots through each of the side ports. In various embodiments, each chamber shaft corresponds to an opening at the proximal end for inserting a drug depot as well as a side port at the distal end of the cannula. Each drug depot is contained within its respective chamber, isolated from contact with adjacent drug depots in adjacent chambers.

FIG. 7a illustrates an embodiment of a quadruple barrel cannula assembly for delivering four drug depots to four delivery sites. In various embodiments the quadruple barrel cannula assembly comprises a tip 705 at the distal end of the cannula, four side ports 710 for expelling four drug depots at the delivery sites, a cannula shaft 715, index markers 720, to indicate the positions of each of the side ports beneath the skin such that the location of each of the four ports beneath the skin is represented by a corresponding index marker located at the proximal end 725 of the cannula assembly visible to the user. Note there are four index markers for a quadruple barrel cannula.

FIG. 7b illustrates an embodiment of the top view of the proximal end 725 of a cannula assembly in the drug delivery device. In various embodiments, the proximal end has four openings or chambers 735 shown as a, b, c, and d, each configured to receive a drug depot for delivery at the delivery sites beneath the skin. In various embodiments, the index markers 720 protrude from the cannula (shown as a', b', c' and d') so that they are visible to the user throughout the procedure. For example, in FIG. 7b, the index marker 720 can be parallel to the drug chambers or channels indicated as a, b, c, and d of 735. The index marker shown as 720, a', b', c', and d' will be parallel to each drug chamber or channel respectively (shown as 735 a, b, c, and d). By looking at index marker 720 a', 720 b', and 720 c', the user will know the position of the drug chamber or channel 735 a, 735 b, and 735 c, respectively.

The user will also know the position of the side port openings (two shown as a and b in FIG. 7c) and thus will know the angle that the drug depot will be dispensed and the position of the side port openings by viewing index marker 720.

FIG. 7c illustrates an embodiment of the cannula shaft 715. In various embodiments, the side ports (two shown as 710 *a*, and *b*), at the distal end of the cannula, are some distance away from the tip of the cannula 705. In various embodiments the distance between the side port and the tip may be between 1-10 mm. In various embodiments the shaft of the cannula is hollow creating four chambers for the passage of the drug depots to the delivery sites. In various exemplary embodiments, a drug inserted into opening 735 *a* of FIG. 7B, would travel through the cannula shaft via the first chamber (735 *a* in FIG. 7*b*) and be dispensed through side port 710 *a* of FIG. 7*c* at a first drug delivery site. In various embodiments, a plunger may be used to facilitate delivery of the drug depot through the cannula shaft and out the side port to the drug delivery site. In various embodiments having four chambers for dispensing four drug depots, the plunger would be appropriately configured to provide four plunging tips (not visible) to dispel the drug depots in chambers a, b, c, and d of FIG. 7*b* through each of the side ports. In various embodiments, each chamber shaft corresponds to an opening at the proximal end for inserting a drug depot as well as a side port at the distal end of the cannula. Each drug depot is contained within its respective chamber, isolated from contact with adjacent drug depots in adjacent chambers.

In various embodiments, the cannula assemblies comprising multiple chambers for delivery of one or more drug depots, delivery of the drug depots may be either simultaneous or sequential. In exemplary embodiments, simultaneous delivery may be effected using a plunger configured to engage multiple plunging tips simultaneously. In various embodiments, each plunging tip aligns with an opening at the proximal end of the cannula, corresponding to a chamber in the shaft of the cannula and a side port at the distal end of the cannula. In an exemplary embodiment, when one plunging tip is inserted into an opening, all of the plunging tips are inserted into an opening, such that all plunging tips are slideably received through their respective openings and into their respective chambers in the shaft of the cannula at the same time.

In various exemplary embodiments where delivery is to be done sequentially, a single plunger having a single plunging tip may be used to dispel the drug depot in one chamber, such that the plunging tip is then slideably removed from the spent chamber and reinserted into a second chamber containing a second drug depot for delivery at a second location beneath the skin. In various embodiments, delivery of a drug depot may be repeated at a single location by reloading the chamber with a subsequent drug depot. In various embodiments, multiple drug doses may be delivered to one or more location without the need to reposition the location of the needle.

Various embodiments may employ a housing structure coupled to the proximal end of the cannula suitable for affixing other components to the delivery device. In various embodiments employing a housing structure, the housing structure would be configured such that a plunger inserted through the top of the housing would be properly aligned with the chambers in the cannula to allow drug delivery in the same manner as if the housing were not present. Various embodiments utilizing a housing structure may also employ the use of a drug cartridge configured to connect to the housing such that simultaneous or sequential delivery to one or more drug delivery sites beneath the skin is possible In various embodiments one or more viscous drugs may be delivered simultaneously or sequentially through the chambers of the cannula shaft to one or more drug delivery sites beneath the skin. In various embodiments, a plunger is not need to facilitate delivery of the drug to the deliver site. The cannula shaft may be continuous (single chamber) with multiple distal side ports. In various embodiments one or more viscous drugs may be delivered simultaneously or sequentially through the single chamber of the cannula shaft to multiple sites below the skin.

Cannula or Needle

The cannula or needle of the drug depot device is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be blunt, beveled, diamond point, ball tip, trocar tip, etc. The cannula or needle may also have a tip style vital for accurate treatment of the patient depending on the site for implantation. Examples of tip styles include, for example, Trephine, Coumand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks. In various embodiments, the distal end of the cannula has one or more side ports for dispensing a drug depot at a delivery site. In various embodiments, the one or more side ports are located a distance away from the tip. In various embodiments the distance between the tip and the closest edge of the side port may range from 1-10 mm.

The cannula or needle of the drug depot device has a diameter that is larger than the diameter of at least part of the plunger (e.g., tip, middle, etc.) to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments the hollow body of the cannula is divided to form two or more chambers inside the cannula. The dividing walls forming each chamber may be of a similar composition of that of the cannula. Each chamber capable of storing a drug depot. Each chamber has an opening at the proximal end to receive a plunger as well as an opening at the distal end to dispel a drug depot. Multiple chambers of the cannula will allow for the simultaneous passage of one or more drug depots through the cannula to one or more delivery sites without interaction between the drug depots.

In various embodiments, the plunger, cannula or drug depot include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, surrounding the opening of the proximal end of the cannula or needle is a generally cylindrical hub having an engagement means for engaging the housing. Engagement means include, but are not limited to, threading, tracks, clips, ribs, projections, and the like that allow a secure connection between the housing and the proximal end of the cannula. For example, in various embodiments the engagement means may be a luer lock connection, where the cannula has mating threads that mate with the threads disposed on or in the housing.

Housing

The housing may be of various shapes including, but not limited to, cylindrical or round such that the housing allows for the affixation to the cannula as well as the plunger. The housing may also be configured for affixation to other components such as, for example a drug cartridge and an electronic nerve sensing unit.

The housing may comprise a variety of materials, such as, for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

Like the cannula or needle, in various embodiments, the housing may have dose indicator markings (e.g., numbers, lines, letters, radiographic markers, etc.) to indicate the number of drug depots delivered. In various embodiments, the plunger includes markings that indicate location at or near the site beneath the skin.

The housing may have contours and allow easy grasping of the device during use. The housing can be angled for right and left hand users or can be generic for both hands. In various embodiments, the housing can comprise an upper opening, a middle opening, and a lower opening. The upper, middle and lower openings allow a plunger to slide through the openings. The middle opening of the housing, in various embodiments, will receive the drug cartridge or the drug depot. In various embodiments, the user can align the drug depot or the chamber of the drug cartridge containing the drug depot with the upper middle and lower openings so that the plunger can pass through and deliver the drug depot.

Plunger

It will be understood that the top end of the plunger may employ a knob, dial, cap, handle or any member that allows the user to utilize the plunger. The plunger has a second end that includes a tip, which is capable of moving the drug depot within the cannula. In other embodiments, the tip of the plunger is sufficiently pointed so that it is capable of insertion to the site beneath the skin of the patient and the cannula or needle is blunted and used to guide the drug depot to the site.

The plunger may be configured to employ multiple tips. The plunger may comprise a single handle having one or more tips attached thereto. The single handle will permit a user to simultaneously insert each of the multiple tips to dispense a drug depot through the cannula. A plunger having multiple tips will best be used in connection with a housing and/or a cannula designed to receive multiple plunger tips for simultaneous distribution of a drug depots. The number of plunger tips will correlate with the chamber design of cannula as well as any housing and drug cartridge that may be used. The each plunger tip is capable of alignment with each of the housing, drug cartridge and cannula chamber that is employed with the delivery of the drug depot.

The plunger has a diameter less than the cannula or needle so that it can be slidably received therein. The plunger may be longer, the same size, or smaller in length than the cannula or needle. In some embodiments, the tip of the plunger can be sharp or blunt.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the number of drug depots delivered. In various embodiments, the plunger includes markings that indicate location at or near the site beneath the skin.

The plunger tip, which may be a complementary shape to the drug pellet, allows the plunger tip to snuggly fit within the end of the drug pellet for easier drug delivery. The drug pellet may have a rounded end for easier insertion at the desired site.

Nerve Sensing Unit

In various embodiments, an electronic nerve sensing unit is incorporated into the drug delivery device (e.g., cannula or needle, housing, etc.). The electronic nerve sensing unit is capable of sensing the presence of a nerve in close proximity to the drug delivery location and alerting the user so the pellets can be implanted as close as possible to the nerve improving the efficacy of the drug eluting pellets. In various embodiments, an electronic device similar to a twitch monitor may be incorporated into the drug delivery device. Suitable nerve sensing units are described in U.S. Pat. Nos. 5,928,158, 5,131,401, and 5,391,081. The entire disclosures of these patents are herein incorporated by reference into the present disclosure.

Other suitable devices include for example, the NIM-ECLIPSE™ Spinal System and NIM-SPINE® System Neural Integrity Monitor (NIM) and nerve monitoring systems disclosed in U.S. Pat. No. 5,196,015, entitled "Procedure for Spinal Pedicle Screw Insertion", and U.S. Pat. No. 5,474,558, entitled "Procedure and System for Spinal Pedicle Screw Insertion" and U.S. Pat. No. 6,554,778, entitled "Biopsy Device with Reuseable Handle." These patent disclosures are also herein incorporated by reference into the present disclosure.

Various embodiments may also include an electronic monitor to track other information measures such as stimulus type, stimulus range, cannula tip sensitivity, amplitude, time, etc.

In some embodiments, the nerve sensing unit (including conductive material, alarms, audio equipment, wires etc.) may be disposed within the housing or outside of the housing as long as it allows conduction of the electrical impulse from the nerve site.

In various embodiments, the patient is connected to a Medtronic NIM stimulator and when the device, which is also connected to the NIM circuitry, touches a nerve it closes the circuit and notifies the user with a light and/or audible signal that the needle tip has contacted the nerve. The user now can implant the drug depot at or near to the nerve.

In various embodiments including an electronic nerve sensing unit, the main electronic component of the unit may be incorporated into the housing of the drug delivery device. The electronic sensing unit may incorporate an electrical contact at the distal end of the cannula near the tip. The contact is capable of electronic communication with the nerve sensing unit and is capable of indicating close proximity to a nerve location. Furthermore, in various embodiments, the nerve sensing unit is capable of electronically signaling an alarm device to alert the user of close proximity to a nerve. The alarm may provide audio, visual, or combination notification to the user.

In various embodiments including an electronic nerve sensing unit, the unit may be electronically coupled to any of a variety of devices including a power supply, user control switches, a stimulation device, and/or an external monitoring device. In various embodiments the power supply may e.g., supply power to the alarm feature. In various embodiments the user may control the sensitivity of the contacts using one or more control switches. Further, in various embodiments, the contact is capable of providing a stimulation signal to a location to detect a nerve, detecting a response signal from a nerve, or stimulating a nerve and sensing a response.

For example, electronic stimulation of the nerve can be accomplished by sending 1, 2, 3, 4, 5, 6, 7, 8, 9, 10 mA of current into the nerve and watching for muscle movement. Alternatively, electronic stimulation can be accomplished by sending 1, 2, 3, 4, 5, 6, 7, 8, 9, 10 mA of current into the nerve or region surrounding the nerve. If there is conductivity, then the user knows that he/she is approaching a nerve.

In some embodiments, the nerve sensing unit may comprise a wire or electrical conducting material running from the tip or distal end of the cannula to a sound and/or visual device that conducts the electrical impulses (e.g., 40 to 90 millivolts (mV)) from the nerve to the sound and/or visual device. In this embodiment, as the user contacts the nerve with the tip of the cannula, the nerve impulse will be conducted through the cannula, through the wire and to the sound and/or visual device, which will alert that user with a visual and/or audio signal that the tip has now contacted a nerve. In this way, the pellets can be placed in close proximity to the nerve improving the efficacy of the drug eluting pellets. The plunger now can slide within the cannula and the drug depot can be delivered out the distal end. In this way, the drug depot can be delivered at or close to the nerve. Thus, direct local treatment of the nerve and the tissue surrounding the nerve can be accomplished.

The nerve can include for example, cranial nerves, central nerves, peripheral nerves, and/or autonomic nerves. Some example of nerves include, for example, a spinal cord nerve, a pelvic nerve, a pudendal nerve, a sacral nerve, a peripheral nerve, a sciatic nerve, or the like.

Drug Depot

In various embodiments, the device comprises a drug depot. A drug depot comprises a physical structure to facilitate implantation and retention in a desired site (e.g., a synovial joint, a disc space, a spinal canal, a tissue of the patient, etc.). The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 mm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[–4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof, protein inhibitors of TNF, such as etanercept, Remicade, IL-1, such as Kineret®, p38, RANK, RANKL.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, coating, matrices, wafers, pills, pellets or other pharmaceutical delivery compositions. In various embodiments, the depot may comprise a bioerodible, a bioabsorbable, and/or a biodegradable biopolymer that may provide immediate release, or sustained release of the drug. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ,-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide (PLA), polyglycolide (PGA), D-lactide, D,L-lactide, L-lactide, D,L-lactide-ϵ-caprolactone, D,L-lactide-glycolide-ϵ-caprolactone or a combination thereof.

In various embodiments, the drug depot comprises drug pellets loaded with a therapeutically effective amount of the therapeutic agent, wherein the pellets are injected into a synovial joint, a disc space, a spinal canal, or a soft tissue surrounding the spinal canal. In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In one exemplary embodiment, the drug depot is in the form of a pellet. The pellet can be any shape, such as for example, bullet shaped, spherical, substantially spherical, flaked, rod shaped, square, oval, etc. The proximal end of the drug pellet may allow the plunger tip to snuggly fit within the proximal end of the drug pellet for easier drug delivery. The distal end of the drug pellet may be rounded for easier insertion at the site.

In various embodiments, the drug pellet comprises a bullet-shaped body that is made from a biodegradable material. In alternative embodiments, the body of the pellet may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from about 1 mm to 5 mm in length and have a diameter of from about 0.01 to about 2 mm. The layer or layers will each have a layer thickness of from about 0.005 to 1.0 mm, such as, for example, from 0.05 to 0.75 mm. The drug depot chambers are often larger than the drug depot dimensions to keep the drug depot within the drug chamber.

Like the cannula, needle, or plunger, in various embodiments, the drug depot (e.g., pellet, cartridge, etc.) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Drug Cartridge

In various embodiments, the drug depot is stored in a drug cartridge. The drug cartridge comprises one or more chambers, each chamber capable of storing a drug pellet. Each chamber isolates the drug pellet from contact with other drug pellets contained within the cartridge. In this way, overcrowding or multiple pellets in one chamber of the drug cartridge is avoided. Further, drug pellets falling out of the drug cartridge due to limited space in the cartridge is also avoided.

In various embodiments, the drug cartridge is capable of insertion into the housing such that the plunger drug cartridge and the cannula are aligned for delivery of the drug depots. In various embodiments involving simultaneous delivery of multiple drug depots through the cannula, the drug cartridge may be any shape or size that allows for the chambers of the drug cartridge containing the drug depots to be aligned with the chambers of the cannula for delivery of the drug depots to the delivery site. In various embodiments, the drug cartridge is round or linear and is slidably receivable through an opening of the housing such that the cartridge is perpendicular to the housing and to the plunger. To deliver the drug depot, the cartridge is inserted into the housing to align with cannula and plunger. The plunger then slides through the housing and the cartridge forcing the drug depot from the cartridge through the cannula to deliver the drug depot to the target site. In various embodiments, the cartridge comprises superior and inferior covers to contain the drug pellet in the chambers to avoid slippage of the pellets from the cartridge.

In various embodiments, the drug cartridge may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high nonferrous metal content and a low relative proportion of iron, carbon fiber, glass fiber, plastics, ceramics or a combination thereof. In various embodiments, the drug cartridge is not biodegradable.

In some embodiments, the drug cartridge comprises multiple drug chambers, where each chamber comprises one drug depot. In various embodiments the number of chambers will be consistent with the number of chambers in the cannula and the number of drug depots selected for simultaneous delivery.

In various embodiments, the drug depot is secured within a chamber by a superior surface to cover the top of the drug cartridge and an inferior surface to cover the bottom of the drug cartridge. The superior and inferior covers keep the drug depot in place preventing the drug depot from slipping from the cartridge. In various embodiments, the superior and inferior covers are made of a thin layer of material that can be penetrated and can be cored by the plunger and/or depot in order to release the drug depot. In various embodiments the penetrable material may comprise, for example, a bioerodible, a bioabsorbable, and/or a biodegradable biopolymer. Examples of suitable materials include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), mPEG, poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ε-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), wax, agar, agarose, gel-vitamin or combinations thereof. In various embodiments, the superior and/or inferior covers comprise poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

The drug device components (e.g., cannula or needle, plunger, housing, engagement means, etc.) may be lightweight, disposable and sterilizable such that when the device is assembled (e.g., the drug cartridge is attached to the housing), the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the cannula or drug cartridge are pre-loaded with the drug depot. This is advantageous when dealing with multi-dose drug pellets that are relatively small (e.g., 1 mm to 5 mm), the user typically cannot grasp these small pellets and load them into the device. By providing them pre-loaded in a cannula or drug cartridge, the user does not have to substantially manipulate the individual drug pellets and the risk of contaminating the pellets particularly with sterilized pellets is reduced.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In some embodiments, the housing, drug cartridge, and/or cannula are transparent so the user can see the position of the plunger and/or the drug depot in the chamber of the drug cartridge. Thus, indicator markings, in this embodiment, are not needed.

In various embodiments, a kit is provided which may include additional parts along with the drug depot device combined together to be used to implant the drug depot. The kit may include the drug depot device in a first compartment. The second compartment may include the drug cartridge, and any other instruments needed for the implant, such as contact leads for nerve sensing unit. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, bone muscles, and the like.

In various embodiments, the drug depot device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots in a quantity of pharmaceutical composition that can be deposited at the target site as needed for treatment of pain, inflammation or other disease or condition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A device for directional placement of a drug depot at a delivery site beneath the skin of a patient, the device comprising:
    a cannula having a proximal end and a distal end, the proximal end of the cannula having an opening to receive the drug depot, the distal end of the cannula capable of insertion to the delivery site beneath the skin of the patient and having a plurality of side port openings for passage of the drug depot, wherein the proximal end further comprises an index marker to provide a visual indicator to a user of a location of the plurality of side port openings, wherein the cannula comprises a plurality of chambers for holding a plurality of drug depots, the plurality of chambers aligned with the plurality of side port openings for drug depot delivery;
    a housing having a coupling means for coupling the proximal end of the cannula to the housing and a storage component configured for storing the drug depot; and
    a plunger having a handle and a tip adapted for dispensing the drug depot, wherein the tip of the plunger is slidably receivable within each of the housing, storage component and the cannula to deliver the drug depot out the side port opening to the delivery site beneath the skin of the patient and the tip of the plunger has a diameter that is smaller than the diameter of the housing, the storage component and the cannula, and the distal end of the cannula comprises a blunt tip.

2. A device for directional placement of a drug depot according to claim 1, wherein the coupling means comprises threading disposed around the housing which is adapted to receive a threading disposed around the proximal end of the cannula.

3. A device for directional placement of a drug depot according to claim 1, wherein the housing comprises a nerve sensing unit comprising an electrical contact and an alarm coupled to the nerve sensing unit such that when the distal end of the cannula is in close proximity to a nerve or contacts a nerve, the alarm is activated.

4. A device for directional placement of a drug depot according to claim 3, wherein the alarm is audible or visible or audible and visible.

5. A device for directional placement of a drug depot according to claim 1, wherein the storage component comprises a chamber and a drug depot stored within the chamber of the storage component.

6. A device for directional placement of a drug depot according to claim 1, wherein one or more drug depots may be sequentially delivered to the site beneath the skin of the patient.

7. A device for directional placement of a drug depot according to claim 1, wherein the cannula comprises two or more side port openings disposed at the distal end for dispensing two or more drug depots to two or more different delivery sites beneath the skin of the patient.

8. A device for directional placement of a drug depot according to claim 7, wherein the plunger comprises two or more plunger tips that align with the two or more side port openings for delivery of the two or more drug depots to the two or more different delivery sites beneath the skin of the patient.

9. A device for directional placement of a drug depot according to claim 8, wherein the proximal end of the cannula has two or more openings, each opening capable of receiving a drug depot and two or more side port openings on the distal end of the cannula, each of the side port openings capable of dispensing a drug depot to the two or more different delivery sites beneath the skin of the patient.

10. A device for directional placement of a drug depot according to claim 9, wherein the drug depots may be simultaneously delivered to the drug delivery sites.

11. A device for directional placement of a drug depot according to claim 1, wherein the site is at least one muscle, ligament, tendon, cartilage synovial joint, bone, spinal disc, spinal canal, or a soft tissue surrounding the spinal canal.

12. A device for directional placement of a drug depot according to claim 1, wherein the drug depot is a sterilizable and biodegradable drug pellet.

13. A device for directional placement of a drug depot at a delivery site beneath the skin of a patient, the device comprising:
a cannula having a proximal end and a distal end, the proximal end of the cannula having an opening to receive the drug depot and a nerve sensing unit comprising an electrical contact and an alarm coupled to the nerve sensing unit, the distal end of the cannula capable of insertion to the delivery site beneath the skin of the patient and having a plurality of side port openings for passage of the drug depot, wherein when the distal end of the cannula is in close proximity to a nerve or contacts a nerve, the alarm is activated; and a plunger having a handle and a tip adapted for dispensing the drug depot, wherein the tip of the plunger is slidably receivable within the cannula to deliver the drug depot out the plurality of side port openings to the delivery site beneath the skin of the patient, the cannula comprises a plurality of chambers for holding a plurality of drug depots, the plurality of chambers aligned with the plurality of side port openings for drug depot delivery for drug depot delivery, wherein the tip of the plunger has a diameter that is smaller than the diameter of the cannula, and the distal end of the cannula comprises a blunt tip.

14. A device for directional placement of a drug depot according to claim 13, wherein the proximal end of the cannula further comprises an index marker to provide a visual indicator to a user of a location of the side port opening.

15. A device for directional placement of a drug depot according to claim 13, wherein the cannula comprises two or more side port openings for dispensing two or more drug depots to two or more different delivery sites beneath the skin of the patient.

16. A device for directional placement of a drug depot according to claim 15, wherein the plunger comprises two or more plunger tips that align with the two or more side port openings for delivery of the two or more drug depots to the two or more different delivery sites beneath the skin of the patient.

17. A method of directional placement of a drug pellet to a site beneath the skin of a patient, the method comprising: positioning a cannula at the site beneath the skin, the cannula having a proximal end and a distal end, the proximal end of the cannula having an opening containing a drug pellet and a nerve sensing unit comprising an electrical contact and an alarm coupled to the nerve sensing unit, the distal end of the cannula capable of insertion to the site beneath the skin of the patient and having a plurality of side port openings for passage of the drug pellet and a blunt tip spaced a distance from the side port opening of the distal end of the cannula, wherein when the blunt tip is in close proximity to a nerve or contacts a nerve, the alarm is activated; and inserting a plunger into the proximal opening of the cannula, the plunger having a handle and a tip adapted for delivering the drug pellet from the plurality of side port openings of the cannula, wherein the cannula comprises a plurality of chambers for holding a plurality of drug pellets, the plurality of chambers aligned with the plurality of side port openings for drug pellet delivery, wherein the tip of the plunger is slidably receivable within the cannula to deliver the drug pellet out of the side port opening to the site beneath the skin of the patient, wherein the diameter of the tip of the plunger is smaller than the diameter of the cannula, and the distal end of the cannula comprises a blunt tip.

18. A method according to claim 17, further comprising sliding the plunger within the cannula to deliver the drug pellet to the site beneath the skin of the patient.

19. A method according to claim 17, further comprising removing the plunger from the cannula, loading a second drug pellet within the proximal end of the cannula, reinserting the plunger and sliding the plunger within the cannula to deliver the second drug pellet to the site beneath the skin of the patient.

20. A device for delivery a drug depot at or near a nerve site beneath the skin of a patient, the device comprising:
a cannula having a proximal end and a distal end, the proximal end of the cannula having an opening to receive the drug depot, the distal end of the cannula capable of insertion to the nerve site beneath the skin of the patient and having a plurality of openings for passage of the drug depot; a plunger being slidably receivable within the opening of the proximal end of the cannula, the plunger having a first end and a tip at a second end, the first end being capable of moving the tip of the plunger to an extended position; a nerve sensing unit disposed on or within the device, the nerve sensing unit comprising an electrical contact material configured to receive electrical impulses from the nerve site so as to detect the nerve, wherein the tip of the plunger has a diameter that is smaller than the diameter of the cannula, and the distal end of the cannula comprises a blunt tip, wherein the cannula comprises a plurality of chambers for holding a plurality of drug depots, the plurality of chambers aligned with the plurality of openings for drug depot delivery.

21. A device for delivering a drug depot according to claim 20, wherein the electrical contact material is disposed at or in a tip of the distal end of the cannula.

22. A device for delivering a drug depot according to claim 20, wherein the device further comprises a housing, wherein the housing has the nerve sensing unit disposed on or in the housing.

23. A device for delivering a drug depot according to claim 20, wherein the nerve site comprises the sciatic nerve.

24. A device for delivering a drug depot, according to claim 20, wherein the nerve site comprises at least one muscle, ligament, tendon, cartilage, synovial joint, spinal disc, spinal foraminal space, near the spinal nerve root, facet joint or spinal canal.

* * * * *